(12) United States Patent
Margraf et al.

(10) Patent No.: US 8,830,473 B2
(45) Date of Patent: Sep. 9, 2014

(54) DEVICE FOR REFERENCED MEASUREMENTS OF REFLECTED LIGHT AND A METHOD FOR CALIBRATING SUCH A DEVICE

(75) Inventors: Joerg Margraf, Jena (DE); Peter Lamparter, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 36 days.

(21) Appl. No.: 13/486,571

(22) Filed: Jun. 1, 2012

(65) Prior Publication Data

US 2012/0314219 A1 Dec. 13, 2012

(30) Foreign Application Priority Data

Jun. 9, 2011 (DE) .......................... 10 2011 050 969

(51) Int. Cl.
*G01N 21/47* (2006.01)
(52) U.S. Cl.
USPC .......................................... 356/446; 356/445
(58) Field of Classification Search
CPC ............... G01N 21/474; G01N 21/255; G01N 21/4785; G01N 2021/4754; G01N 2021/4783; G01N 2021/8427; G01N 21/59; G01N 21/8422; G01N 21/896; G01N 2201/065
USPC ........... 356/446, 237.1–237.6, 236, 445, 244, 356/222, 448; 250/228, 236, 237 R
See application file for complete search history.

(56) References Cited

U.S. PATENT DOCUMENTS

| | | | |
|---|---|---|---|
| 3,458,261 A | 7/1969 | Bentley et al. | |
| 4,575,252 A | 3/1986 | Akiyama | |
| 4,756,619 A | 7/1988 | Gerlinger et al. | |
| 4,900,923 A | 2/1990 | Gerlinger | |
| 5,182,618 A | 1/1993 | Heinonen | |
| 5,764,352 A | 6/1998 | Kappel et al. | |
| 8,259,294 B2 * | 9/2012 | Proehl et al. | ................. 356/236 |
| 2001/0055116 A1 | 12/2001 | Maczura et al. | |

FOREIGN PATENT DOCUMENTS

| | | |
|---|---|---|
| DE | 16 22 484 | 11/1973 |
| DE | 33 38 203 A1 | 5/1984 |
| DE | 3526553 | 1/1987 |
| DE | 195 28 855 A1 | 2/1997 |
| DE | 10 2009 040 642 | 3/2011 |
| DE | 10 2010 041 749 A1 | 4/2012 |
| EP | 0344645 A2 | 12/1989 |
| GB | 2366372 | 3/2002 |
| WO | WO 2012/042015 | 4/2012 |

OTHER PUBLICATIONS

German Search Report, with English translation, for corresponding DE Appl No. 10 2011 050 969.0, dated Jan. 27, 2012.
European Search Report , EP1217124, dated Oct. 24, 2012.

* cited by examiner

*Primary Examiner* — Tri T Ton
(74) *Attorney, Agent, or Firm* — Fish & Richardson P.C.

(57) ABSTRACT

A device includes a hollow body having a light-exit opening configured to illuminate a specimen, an interior of the hollow body comprising a diffusely scattering layer. The device also includes a light source configured to illuminate the diffusely scattering layer, a first photo-detector aligned along a first detection axis, and a second photo-detector aligned along a second detection axis. The device is configured to measure referenced measurements of reflected light.

26 Claims, 7 Drawing Sheets

DEVICE FOR REFERENCED MEASUREMENTS OF REFLECTED LIGHT AND A METHOD FOR CALIBRATING SUCH A DEVICE

CROSS-REFERENCE TO RELATED APPLICATION

This application claims priority under 35 U.S.C. §119 to German Application No. 10 2011 050 969.0, filed Jun. 9, 2011. The contents of this application are hereby incorporated by reference in their entirety.

FIELD

The disclosure relates to a device for the measurement of light reflected on a specimen. The device includes a hollow body having a light-exit opening for illuminating the specimen and, in its interior, a diffusely scattering layer. The device also includes a light source for illuminating the layer, a first photo-detector aligned along a first detection axis, and a second photo-detector aligned along a second detection axis. The disclosure also relates to a method for calibrating such a device.

BACKGROUND

For the purposes of the disclosure, the term light refers to any electromagnetic radiation that can be manipulated by optical devices, such as ultraviolet light, visible light, and infrared radiation. The detection axis of a photo-detector can be, for example, the symmetry axis of a field of vision, such as the optical axis of the photo-detector. In terms of geometry, it is a spatial line which begins in that photo-detector. Each photo-detector may be, for example, either end of an optical fiber or bundle, in particular including an optical exciting probe. The optical fiber(s) then lead, for example, to an optoelectronic transformer, such as a spectrometer. A spectrometer includes, for example, an entrance slit, a diffracting element, such as a grating, and an optoelectronic transformer, as well as, optionally, a control unit.

A measuring device of the type described above is known, for example, from DE 195 28 855 A1, the entire disclosure of which is incorporated herein by reference, in particular regarding the detection of the spectral energy distributions Φ and of the luminance factor functions β. The light from the light source scattered on/in the inner layer can exit from the hollow body through the light-exit opening. At a specimen located in front of the light-exit opening, the light is remitted, at least partially, to the light-exit opening (back-scattered and/or reflected there) so that it re-enters the hollow body. A first photo-detector is provided for detecting this light (measurement light, in which properties of the specimen are encoded) that is diffusely reflected into the hollow body; a second photo-detector is provided for the detection of the light that is scattered within the hollow body on/in the diffusely scattering layer (reference light, in which are encoded the properties of the light source). The inclusion of the reference light serves to determine the spectral energy distributions measured in reflection and/or transmission regardless of short-term fluctuations of the wavelength-dependent optical transmission properties of the detection beam path and the emission characteristics of the light source.

Such measuring devices are used, among other applications, in manufacturing and/or in the quality control of optical products. Here, it is often desirable to measure optical properties, for example, reflection and/or transmission behavior, as a function of the wavelength of the light. An example of this is the optical analysis of filter layers acting as an infrared filter, which block heat radiation but should allow visible light to pass as unimpededly as possible. Such filter layers are applied, for example, to architectural glass or automotive glass. Another example are anti-reflective coatings, in particular for broadband antireflection, which should have the lowest possible reflection within the range of visible light. Measurements of their spectral dependence is desired both during the manufacturing process of such coatings and as part of the final quality control of their optical properties.

In order to determine the spectral energy distributions of the specimen surfaces of interest that are measured in reflection and/or transmission regardless of long-term changes in the wavelength-dependent optical transmission properties of the detection beam path and the emission characteristics of the light source, it is desirable to calibrate the measuring device by measuring a reference standard in the detection beam path of the measuring device. As a rule, at least one so-called white standard is used, which scatters incoming light diffusely and typically has a maximum reflectance and/or transmission rate at all wavelengths to be measured at the specimen.

To calibrate the measuring devices known to the art, either the reference standard is moved in front of or instead of the specimen into the detection beam path, or the measuring device is moved in parallel into a calibrating position away from the specimen, such as in DE 195 28 855 A1. In all of these cases, due to the relative movement, inaccuracies occur in the positioning of the object that is being moved. Because of this, the reference standard is not always at the same distance from the light-exit opening as the specimen. Also, the inclination of the reference standard relative to the light-exit opening can vary due to this movement. Minor variations in distance or orientation, however, lead to large differences in the measured light intensities, i.e., result in a large error of the calibration measurement. A large error in the calibration is then continued into the specimen measurements.

Also, the relative movement may cause a disturbance of the measuring geometry. For example, the optical properties of optical fibers change when they are moved. In addition, the reference standard in the measuring devices known to the art can become soiled. This can happen in particular due to the monitored manufacturing process, for example, by sputtering. Also, the ambient temperature can affect the reference standard in the measurement devices known to the art. The accuracy of the calibration can be significantly affected. In addition, the handling of the reference standard is quite complex if the specimen is used and measured in a vacuum.

SUMMARY

The disclosure provides a device for light measurement, which can be calibrated with higher accuracy, and to propose a calibration method for such a device.

According to a first aspect of the disclosure, the device can be switched from a measuring position to a calibrating position, wherein the light-exit opening lies on the first detection axis (but not on the second detection axis) in the measuring position, and lies on the second detection axis (but not on the first detection axis) in the calibrating position. For the purposes of the disclosure, a statement that the light-exit opening lies on a specified axis means that this axis passes through the light-exit opening. The same applies to the diffusely scattering layer.

In the measuring position, the light-exit opening is arranged so that it illuminates the specimen, and the first photo-detector receives light coming from the specimen through the light-exit opening. In the calibrating position, the light-exit opening is arranged so that it illuminates an alternative measurement site, which lies on the second detection axis, instead of the specimen. The positioning of the photo-detectors and their detection axes remain the same even when switching the positions. Therefore, in the calibrating position, the second photo-detector receives light from the alternative measurement site.

With the same measuring device, one can thus measure at two different measurement sites, without having to move the device to another location. In particular, a reference standard can be arranged at the alternative site, and it can stay there permanently, without the need for it or for the device for measuring the reference standard (including for receiving reference light from the diffusely scattering surface) to be linearly moved. A pre-requisite can be the positioning of the reference standard without disturbing the specimen. This device can therefore be calibrated with higher accuracy than conventional measuring devices.

To achieve particularly high accuracy in measurement and calibration, the distance between the first photo-detector and the light-exit opening in the measuring position can be identical to the distance between the second photo-detector and the light-exit opening in the calibrating position.

Accordingly, advantageous embodiments include those in which a holder for a reference standard is arranged outside the hollow body, or a reference standard is arranged such that the reference standard lies on the second detection axis. This makes it possible to make the distance between the reference standard and the second photo-detector identical to the distance between the specimen and the first photo-detector. This distance can be maintained identical even in later calibration sessions. The same applies to the inclination of the reference standard with respect to the second photo-detector. Due to this arrangement, the device can be calibrated with higher accuracy than conventional devices.

Each of the photo-detectors may be arranged either within the hollow body or outside the hollow body. For each photo-detector arranged outside, the hollow body should include a corresponding detection aperture.

The hollow body may conveniently be formed such that, in the measuring position, a first region of the diffusely scattering layer lies on the second detection axis and that, in the calibrating position, a second region of the diffusely scattering layer lies on the first detection axis. Because of this arrangement, the reference light from the diffusely scattering layer can be received in both positions: in the measuring position via the second photo-detector, in the calibrating position via the first photo-detector. When switching from the measuring position to the calibrating position, the two photo-detectors thus switch their functions. Assuming that the first region and the second region of the diffusely scattering layer have identical reflectance properties, the sensitivity ratio of the first and second photo-detector can be determined with little effort and can be used in the calibration.

The ability to switch between the positions is achieved through effective relocation of the light-exit opening. This can be achieved with little effort, for example, either a) when the light-exit opening can be moved from a position along the first detection axis to a position along the second detection axis and vice versa, or b) when the hollow body includes a reference light-exit opening on the second detection axis, wherein the specimen light-exit opening and the reference light-exit opening can be closed at least alternately.

In case a), the hollow body can be set up, for example, such that the light-exit opening is movable back and forth between a first position, in which the first detection axis extends through the light-exit opening and the second detection axis extends through the diffusely scattering layer, and a second position, in which the first detection axis extends through the diffusely scattering layer and the second detection axis extends through the light-exit opening. In particular, to obtain the ability to be handled like this, the hollow body can be mounted so it can move, in particular rotate. Alternatively, only a section of the hollow body, which includes the light-exit opening, can be movable, for example, a strip extending around the hollow body, while the rest of the hollow body is stationary. Provided that the device includes one or more photo-detectors that are arranged outside the hollow body, the hollow body should advantageously include a number of detection holes for each of these photo-detector corresponding to the number of possible positions. Preferably, each two detection holes of adjacent photo-detectors should be identical to each other.

In case b), the hollow body includes two measurement light-exit openings, wherein the first detection axis extends through the specimen light-exit opening, and the second detection axis extends through the reference light-exit opening. For this purpose, a shutter can be arranged, for example, inside or outside the hollow body, which is movable back and forth between the specimen light-exit opening and the reference light-exit opening. Alternatively, it may be possible to close each light-exit opening independently of the other, for example, by a respective screen, in particular an iris screen.

Conveniently, the first photo-detector is aligned to receive the light coming through the light-exit opening into the hollow body in the measuring position, and the light scattered by the layer in the calibrating position. Conveniently, the second photo-detector is aligned to receive the light scattered by the layer in the measuring position and the light coming through the light-exit opening into the hollow body in the calibrating position.

The first photo-detector is preferably optically designed such that, in the measuring position, it receives the light entering the hollow body through the light-exit opening exclusively. The second photo-detector is preferably optically designed such that, in the measuring position, it receives the light scattered by the inner layer exclusively. For this purpose, the photo-detectors may be equipped, for example, with a respective screen and/or respective lens optics.

Particularly advantageous are embodiments, in which the photo-detectors and the detection axes are fixed in space regardless of these positions. This avoids problems stemming from inaccurate positioning and optical changes by moving optic fibers.

A particularly accurate calibration is made possible by an embodiment, in which an angle formed between the second detection axis in the measuring position and a surface normal of the diffusely reflecting layer at an intersection point of the second detection axis through the layer is identical to an angle formed between the first detection axis in the calibrating position and a surface normal of the diffusely reflecting layer at an intersection point of the first detection axis through the layer. This achieves a measurement geometry which, when measuring the reference standard, is largely identical to the measurement geometry when measuring the specimen in the measuring position.

In particular, in the measuring position, the first detection axis (preferably for only diffusely reflecting specimens) can be identical to a central axis of the light-exit opening, or (preferably for partially directionally reflecting specimens) can form an angle of 8°.

In a particular embodiment, the device can also be switched into a referencing position, in which the first and the second detection axes extend through the diffusely scattering layer. Thus, the relative sensitivity, i.e., the ratio of the sensitivities of the first photo-detector and the second photo-detector, can be determined, for example, by calculating the quotient of the photo-detectors' signal values.

Although the two photo-detectors in the referencing position are oriented to different locations of the layer, but with a sufficiently homogeneous layer, the scattering behavior is the same.

In particular, in the referencing position, a site of the diffusely scattering layer that lies on or near the second detection axis in the measuring position can lie on or close to the first detection axis. For the purposes of the disclosure, "close to" means a distance of less than one diameter of the hollow body's light-exit opening. In this particularly advantageous referencing position, the same region of the diffusely scattering layer can be detected by the first photo-detector, from which the reference light is received by the second photo-detector in the measuring position. This advantageously serves to determine with very high accuracy the relative sensitivity of the first photo-detector and the second photo-detector by receiving light from (at least approximately) the same location of the layer.

In a further advantageous embodiment, the device may include a third photo-detector, aligned along a third detection axis, wherein the device can additionally be switched into an auxiliary calibrating position, in which the light-exit opening lies on the third detection axis, in particular, with the inclusion of a holder for an additional reference standard or of an additional reference standard such that the additional reference standard outside of the hollow body lies on the third detection axis. In the auxiliary calibrating position, the light-exit opening is arranged so that it illuminates a second alternative measurement site. To this end, the hollow body can be manipulated appropriately. If the third photo-detector is arranged outside the hollow body, it includes three detection holes for the third photo-detector, which can partially coincide with other detection holes, if any. In the third position, the third photo-detector can be used to measure the auxiliary reference standard, which is arranged on the third detection axis, particularly such that it can remain there permanently. The auxiliary reference standard may be, for example, a gray standard with a reflectance of 50%. Based on the auxiliary reference standard's reflectance function determined in this manner it would be possible, for example, using a control unit included in the device, to check whether a shutter covering the light-exit opening is significantly dirty. If so, the control unit can issue a visual or audible warning.

Preferably, the hollow body should be mounted so that it can rotate, preferably around exactly one axis of rotation, for the purpose of switching the device between all positions.

According to a second aspect of the disclosure, it is provided that for switching the device from a measuring position to a calibrating position, the hollow body including the light-exit opening and the photo-detectors should be mounted so that it can rotate around an axis different from the first detection axis, wherein the first photo-detector is aligned in both positions for receiving the light entering the hollow body through the light-exit opening, and the second photo-detector is aligned in both positions for receiving the light scattered by the layer.

Using the same measuring device, it is thus possible to measure at two different measurement sites, without having to move the device to another location. In particular, a reference standard can be arranged at the alternative measuring site and can also remain there permanently, without the need for it or for the device measuring the reference standard (including receiving reference light from the diffusely scattering surface) to be linearly moved. A prerequisite can be the (one-time) positioning of the reference standard without disturbing the specimen. The device can thus be calibrated with higher accuracy than conventional measuring devices.

Accordingly, advantageous embodiments are those in which a holder for a reference standard or a reference standard is arranged outside the hollow body such that the reference standard lies on the first detection axis in the calibrating position. This allows setting up the distance between the reference standard and the first photo-detector to be identical to the distance between the specimen and the first photo-detector. This distance can be maintained identical even in later calibration sessions. The same applies to the inclination of the reference standard relative to the first photo-detector.

The variants described below apply to both aspects of the disclosure.

It is advantageous to limit the movement of the hollow body by one or more stops in a defined manner. Particularly with the second aspect of the disclosure, this can avoid fluctuations in the relative orientation of the reference standard and the hollow body.

Advantageously, a shield can be provided between the holder/reference standard on the one hand, and the specimen on the other hand. This arrangement allows protecting the reference standard from the specimen environment. The reference standard can thus be affected less mechanically, which maintains calibration accuracy in the long term. Preferably in such embodiments, the shield includes a casing surrounding the holder/reference standard, which opens towards the hollow body. With this arrangement, the reference standard is especially well-protected. Conveniently, in this case, the light-exit opening of the hollow body is covered by a transparent protective screen. The casing surrounding the reference standard can be particularly protected from the environment surrounding the casing with a seal, which particularly allows the use of the measurement device in a vacuum with little effort, because the reference standard can remain in place even during handling and/or measurements of the specimen.

Alternatively to shielding only the reference standard, the shield can protect the hollow body, the holder/reference standard, and the photo-detectors from the specimen, and it can include a light-exit opening having a transparent protective screen in the area in which the main light-exit opening is located in the measuring position. In this manner, the measuring device, including the reference standard, is protected from the specimen environment.

A particularly high level of protection can be achieved if the shield is a common casing around the hollow body, the holder/reference standard and the photo-detectors. This embodiment can also be used particularly in a vacuum with little effort, because the reference standard can remain in place even during handling and/or measurements of the specimen.

Advantageously, the hollow body can be an integrating sphere or an integrating tube, in particular an integrating tube with several offset parallel pairs of first and second photo-detectors. An integrating tube, like an integrating sphere, is provided everywhere inside except for openings with a diffusely scattering layer; however, in contrast to an integrating sphere, it includes, for example, a translation-invariant cross-section of a finite size, with the exception of openings. Such tubes are referred to in DE 10 2010 041 749 (A1), the disclosures of which are included here as far as possible.

Preferably, both detection axes run through the hollow body. If so, the distance between the specimen and the light-exit opening can be close to zero in the measuring position, which permits very high measurement accuracy.

The device according to the first aspect of the disclosure in all its possible embodiments can be calibrated in that the device is switched into the calibrating position and the light entering through the light-exit opening is received by the second photo-detector as a reference standard spectral energy distribution, and the light scattered by the diffuse layer is received via the first photo-detector as a light source spectral energy distribution, and based on these two spectral energy distributions, a reference standard reflectance function is determined. The wavelength-dependent spectral energy distributions can be determined via a spectrometer installed downstream from the photo-detector. Similarly, the wavelength-dependent reflectance function of the reference standard can be determined.

After a calibration procedure has been performed according to the preceding claim, the device can be later switched to the measuring position, and then the light entering through the light-exit opening can be received by the first photo-detector as specimen spectral energy distribution, and the light scattered by the diffuse layer can be received by the second photo-detector as light-source spectral energy distribution, and the specimen reflectance function can be determined using these two spectral energy distributions and the reference standard reflectance function determined in the calibration procedure. Of course, the calibration procedure can also be performed after one or several measurements have been taken. Conveniently, it is carried out before and afterwards. For example, in order to determine the specimen reflectance function, a reference-standard reflectance function interpolated between the two calibrations is used.

A measurement of the light reflected on a specimen according to the first aspect of the disclosure may generally include the following steps:
1. Positioning a specimen on a first detection axis,
2. Positioning a reference standard on a second detection axis,
3. Positioning a diffusely scattering layer in front of the specimen on the first detection axis,
4. Illuminating the diffusely scattering layer to generate diffused light,
5. Directing a portion of the generated light to the reference standard,
6. Receiving light from the reference standard along the second detection axis as reference-standard spectral energy distribution,
7. Receiving light from the diffusely scattering layer along the first detection axis as light-source spectral energy distribution relative to the reference-standard spectral energy distribution,
8. Removing the diffusely scattering layer from the first detection axis,
9. Positioning the diffusely scattering layer in front of the reference standard on the second detection axis,
10. Directing a portion of the generated light to the specimen,
11. Receiving light from the specimen along the first detection axis as specimen spectral energy distribution, and
12. Receiving light from the diffusely scattering layer along the second detection axis as light-source spectral energy distribution for the specimen spectral energy distribution.

It is alternatively possible to perform the set of steps 3/5/6/7 after the set of steps 9/10/11/12. The sequence of steps 6 and 7 is optional, in particular, they can be performed simultaneously. The same applies to steps 11 and 12. Naturally, illumination (Step 4) desirably is continued at least during the receiving steps (5/6/7 and 10/11/12). The sequence of steps 1, 2 and 3 is optional; in particular, they can be performed simultaneously.

The placement and removing of the layer can be carried out by translation and/or rotation of the layer. Different areas of the layer can be located on the respective detection axis.

The above steps may be performed, for example, by a respective software module. Alternatively, a software module may perform multiple or all steps.

The objective of measurements with one of the described devices is to determine a specimen reflectance factor function. This is achieved by performing the following steps:
determining a reference standard reflectance function based on the reference-standard spectral energy distribution and using the light-source spectral energy distribution relative to the reference-standard spectral energy distribution, and
determining a specimen reflectance function based on the specimen spectral energy distribution and using the light-source spectral energy distribution for the specimen spectral energy distribution.

These steps, too, may be performed, for example, by a respective software module. Alternatively, a software module may perform multiple or all steps.

Conveniently, the reference-standard reflectance function is adjusted to the different sensitivities via the relative sensitivity of the first and the second photo-detector before the specimen reflectance function is determined.

Determining the reference-standard reflectance function based on the reference-standard spectral energy distribution and using the light-source spectral energy distribution relative to the reference-standard spectral energy distribution can be performed at any time after the capture of the reference-standard spectral energy distribution and the light-source spectral energy distribution relative to the reference-standard spectral energy distribution (above, steps 6/7). It is not necessary to perform this immediately prior to the determination of the specimen reflectance function.

Preferably, the light from the reference standard and the light from the specimen is received through a light-exit opening of a hollow body, inside which is arranged the diffusely scattering layer.

In all aspects of the disclosure, the two or three detection axes preferably all lie in the same spatial plane.

The disclosure also includes embodiments in which one or more machine-readable media are configured to store instructions that are executable by one or more processing devices to perform a method disclosed herein. In addition, the disclosure includes an electronic system which includes one or more processing devices and one or more machine-readable media configured to store instructions that are executable by the one or more processing devices to perform operations including a method disclosed herein. The machine-readable media is a tangible medium, such as a memory, hard drive, and/or disk. A processing device is, for example, a computer. The disclosure further includes a control unit configured to perform a method disclosed herein. Moreover, the disclosure includes a system which includes such a control unit and a device as disclosed herein.

The disclosure is particularly suitable for repeated measurements during a continuous production process (in-line), or during the continuous testing of a specimen with a large surface, which continuously passes by the device.

Besides the measurement of light reflected by a specimen, the device may be used alternatively or simultaneously for measuring light transmitted through the specimen. This involves at least one photo-detector on the side of the specimen opposite the light-exit opening. In both aspects of the disclosure, light transmission can only be measured in the measuring position.

BRIEF DESCRIPTION OF THE DRAWINGS

The disclosure will be explained in more detail below using exemplary embodiments. In the drawings.

DETAILED DESCRIPTION

In all drawings, equivalent parts have the same identifying numbers.

Figure 1A:
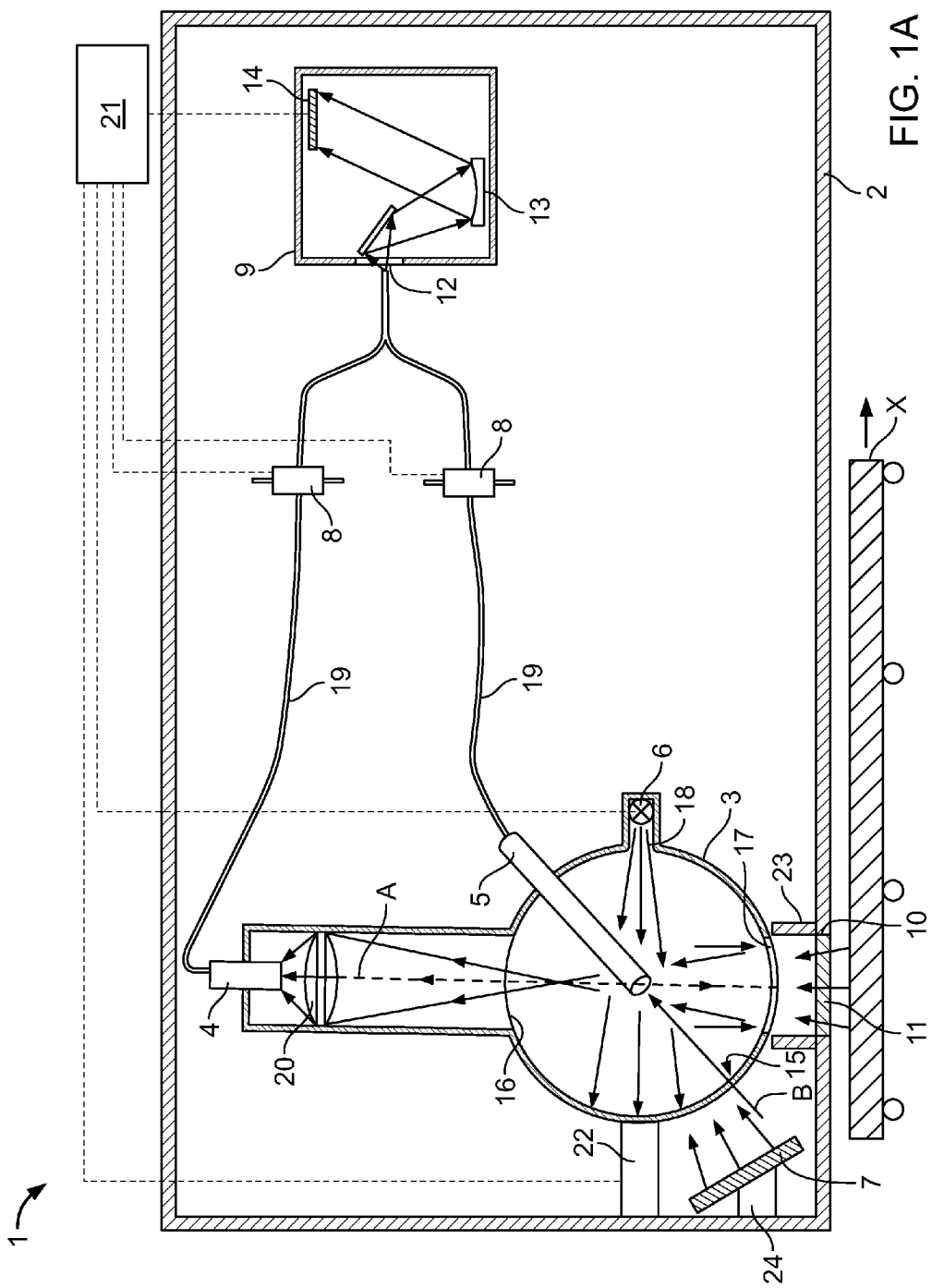
FIG. 1 shows a first measuring device in the measuring position and in the calibrating position.
Figure 1B:
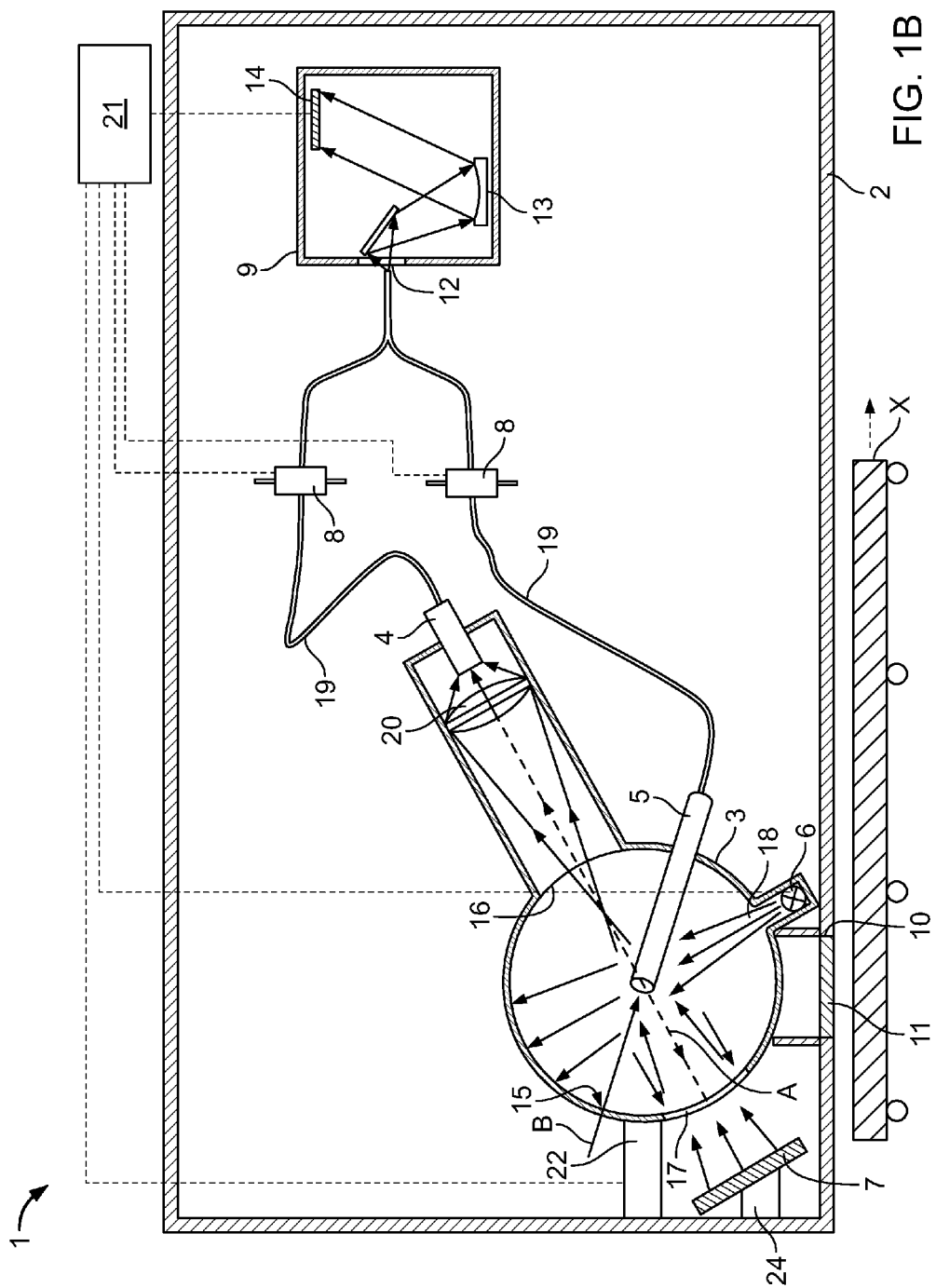

FIG. 1 shows a cross-section of an exemplary measurement device 1 according to the second aspect of the disclosure, which is switchable between a measuring position and a calibrating position. Partial FIG. 1A shows device 1 in the measuring position, partial FIG. 1B shows it in the calibrating position. Device 1 is part of a manufacturing monitoring system, in which a specimen X, for example, coated flat glass, passes by device 1.

Device 1 includes a casing 2, which encases a hollow body 3 in the form of an integrating sphere, a first photo-detector 4 and a second photo-detector 5, each in the form of an exciting probe connected to respective optical fibers, a light source 6, a reference standard 7, two optical shutters 8, and a spectrometer 9. Casing 2 includes a light-passage opening 10 with a transparent protective plate 11. Inside spectrometer 9, an entrance slit 12, an imaging diffraction grid 13, and an opto-electronic detector 14, made of silicon for example, are arranged as an example. The reference standard is arranged in a holder 24.

The hollow body 3 is provided on its inside with a diffusely scattering layer 15, for example, a white coating of barium sulfate, and, for example, includes three openings: a blind stud with the light source 6 for illuminating the layer 15 is connected, as an example, to the light-entry opening 16. The light emitted by light source 6 is diffusely reflected at layer 15, so that the light is scattered in all directions within the hollow body 3, resulting in the diffuse reflection at layer 15 being duplicated many times.

A portion of this scattered light can exit the hollow body 3 through the light-exit opening 17. Depending on the position of device 1, it then passes either to specimen X (measuring position) or to reference standard 7 (calibrating position). From there, it is at least partially remitted back into the hollow body 3 through the light-exit opening 17, where it is received by the first photo-detector 4. Photo-detector 4 is aligned with light-exit opening 17 and receives the portion of the light entering the hollow body through the light-exit opening exclusively. To this end, a convex optical device is arranged in front of the first photo-detector 4. Another portion of the light scattered by layer 15 is received by the second photo-detector 5, which has for example, a tubular shutter arranged in front of it, which is inserted into hollow body 3 through a detector hole 18. The shutter is coated on the outside, for example, with the same diffusely scattering material as is the inside of hollow body 3.

Both photo-detectors 4, 5 are embodied as ends of optical fibers 19, each with optical exciting probes 20. The optical fibers 19 direct the light entering through the closable shutters 8 to the spectrometer 9. Depending on the setting of the shutters 8, spectrometer 9 detects either the measurement light received by the first photo-detector 4, which has entered into the hollow body through the light-exit opening 17, or the reference light received by the second photo-detector 5 from layer 15, which represents the instantaneous light source radiation and is used for compensating for variations in brightness of the light source 6. In spectrometer 9, the light entering through slit 12 is spatially spectrally split by grid 13 and passes to detector 14, where it can be detected spectrally resolved. Detector 14 is connected to a control unit 21, which, besides measuring the values, is equipped for controlling the shutters 8, the light source 6, and the position of device 1 via a drive 22.

Drive 22 is embodied such that the integrating sphere 3 can be rotated around one of its central axes, for example, about the central axis that extends perpendicular to the plane of the drawing. In such a rotation, the photo-detectors 4, 5 rotate together with the hollow body 3, because in the illustrated case, they are firmly affixed to the hollow body 3. Switching from the measuring position to the calibrating position is effected by turning the hollow body 3 via drive 22 such that the light-exit opening 17 and the first detection axis A of the first photo-detector 4, which extends through the light-exit opening 17, are no longer aligned with specimen X, but with the reference standard 7. The second detection axis B also rotates during this movement. Because of this, in this example, the second photo-detector 5 always receives reference light from the same place of the diffusely scattering layer 15, regardless of the position of device 1.

The signals emitted by the first photo-detector 4 in the calibrating position are digitized by the control unit 21 and stored as the reference-standard spectral energy distribution. The signals emitted by the second photo-detector 5 in the calibrating position are digitized by the control unit 21 and stored as light-source spectral energy distribution. From these two functions, the control unit 21 determines the reference-standard reflectance function, for example according to DE 195 28 855 A1.

For measuring the specimen properties, the control unit 21 switches device 1 into the measuring position via driver 22. The first detection axis A then passes through specimen X. The signals emitted by the first photo-detector 4 in the measuring position are digitized by control unit 21 and stored as the specimen spectral energy distribution of the current measurement site. The signals emitted by the second photo-detector 5 in the measuring position are digitized by control unit 21 and stored as light-source spectral energy distribution relative to the specimen spectral energy distribution. Based on these two spectral energy distributions and using the reference-standard reflectance function, control unit 21 determines the specimen reflectance function of the currently measured site, for example, according to DE 195 28 855 A1.

By analyzing the specimen reflectance factor function, the control unit can, for example, monitor the value of a specific specimen property and compare it with a desired value or desired interval. If any deviations are detected, it can record this, for example, and/or give out a visual and/or audible warning.

Casing 2 has, for example, a cylindrical wall section 23, which can be formed, for example, as a light guide device as defined in DE 38 188 15 A1. However, the wall section 23 can also be omitted.

In possible alternative embodiments (not shown), the photo-detectors 4, 5 can be mounted such that they can rotate independent of the hollow body 3, if their axis of rotation is identical to the rotational axis Q of the hollow body 3.

The illustrated embodiment has the disadvantage that the measurements can be affected by the movement of the optical fibers 19 while switching position.

Figure 2A:
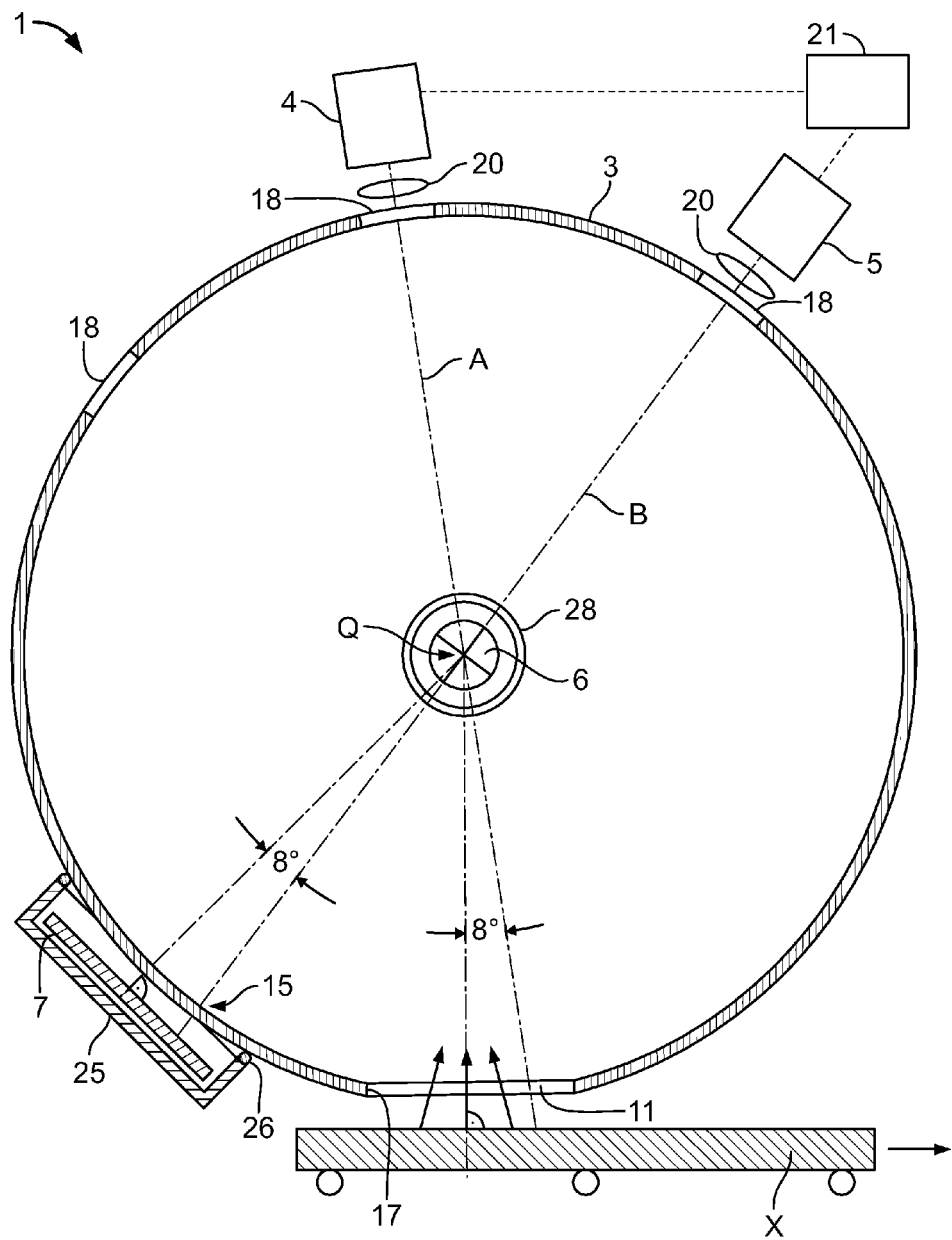
FIG. 2 shows a second measuring device in the measuring position and in the calibrating position.
Figure 2B:
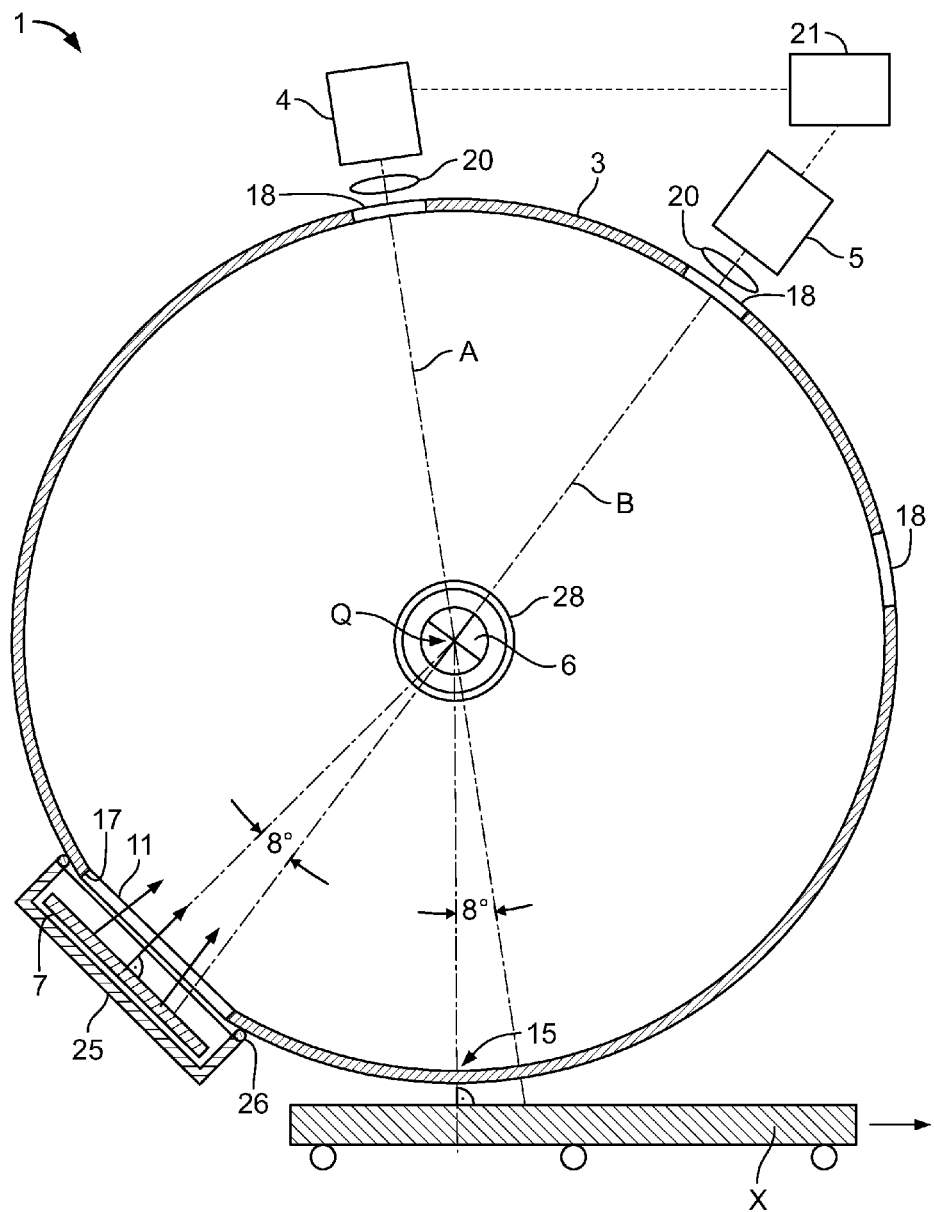
Figure 2C:
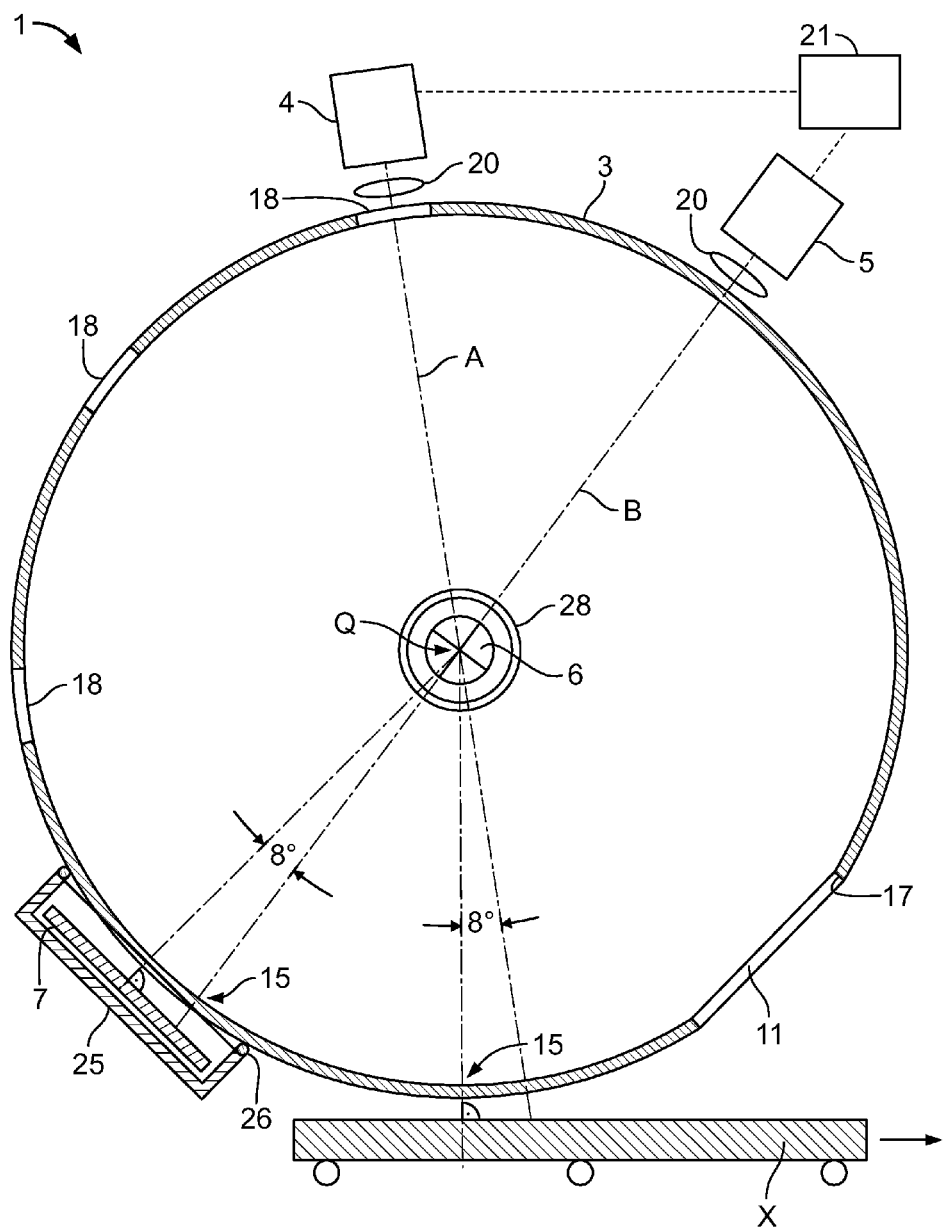

FIG. 2 illustrates a measuring device 1 according to the first aspect of the disclosure in cross-section, which does not have this disadvantage. Partial FIG. 2A shows device 1 in measuring position, partial FIG. 2B in calibrating position, and partial FIG. 2C shows it in reference position. The device 1 is, for example, part of a manufacturing monitoring system, in which a specimen X, for example, coated flat glass, passes by device 1.

Device 1 includes a hollow body 3 in the form of an integrating sphere, a first photo-detector 4, a second photo-detector 5, each in the form of an exciting probe connected to respective optical fibers, a light source 6, and a reference standard 7. A lateral shield 28 is arranged around the light source 6, which prevents light propagating directly from light source 6 to the photo-detectors 4 and 5. The hollow body 3 includes a light-exit opening 17 for illuminating specimen X with diffuse light, which is covered by a transparent protective plate 11. The reference standard is enclosed by a separate casing 25, which is open towards the hollow body 3. Between it and the hollow body 3, a seal 26 is arranged to protect the reference standard against influences from the environment of specimen X. The hollow body 3 is provided on its inside with a diffusely scattering layer 15, for example, a white coating of barium sulfate. The light emitted by light source 6 is diffusely reflected at layer 15, so that the light is scattered in all directions within the hollow body 3, resulting in the diffuse reflection at layer 15 being duplicated many times. A portion of this scattered light can exit the hollow body 3 through the light-exit opening 17. Depending on the position of device 1, it then passes either to specimen X (measuring position) or to reference standard 7 (calibrating position). From there, it is at least partially remitted back into the hollow body 3 through the light-exit opening 17.

Device 1 can be switched between the measuring position and the calibrating position. To this end, the hollow body 3 can be rotated, for example, via the drive shown in FIG. 1 about one of its central axes, for example, about the central axis, which extends perpendicular to the plane of the drawing. In such a rotation, the photo-detectors 4, 5 do not rotate together with the hollow body 3, because they are oriented, at a fixed distance from each other, with spatially fixed detection axes A or B, fixed in space, and oriented in a spatially fixed manner, for example, at an angle of 8° to the specimen normal (first photo-detector) or to the reference standard normal (second photo-detector). The detection axes A and B also remain constant during the switching. Because of the spatially fixed arrangement of photo-detectors 4, 5, the distances between the specimen and the first photo-detector and between the reference standard and the second photo-detector are not only constant regardless of the position of device 1, but, for example, identical.

In the measuring position, the light remitted through the light-exit opening 17 is received by the first photo-detector 4. Photo-detector 4 is aligned along the first detection direction A to the light-exit opening 17 and receives a portion of the light entering through the light-exit opening 17 into the hollow body 3 exclusively. Another portion of the light scattered at layer 15 is received by the second photo-detector 5 along the second direction of detection.

The detection axes A, B of both photo-detectors each extend through a respective detector hole 18 through the hollow body 3. As in FIG. 1, the photo-detectors 4, 5 can be connected with a spectrometer (not shown) that can be switched on or off. The first photo-detector 4 is used for receiving measurement light through the light-exit opening 17, which is used to determine the specimen spectral energy distribution of the current measurement location on the specimen. The second photo-detector 5 serves to receive diffused reference light, which is used to determine the light-source spectral energy distribution relative to the specimen spectral energy distribution.

Switching from the measuring position to the calibrating position is performed by turning the hollow body 3 such that the light-exit opening 17 no longer lies on the first detection axis A, but on the second detection axis B. The first photo-detector 4 is then no longer aligned to specimen X, but to the diffusely scattering layer 15. The second photo-detector 5 is no longer aligned to the diffusely scattering layer 15, but to the reference standard 7. Now the second photo-detector 5 serves to receive measurement light through the light-exit opening 17, which is used to determine the reference standard spectral energy distribution. In contrast, the first photo-detector 5 is now used for receiving diffuse reference light, from which the light-source spectral energy distribution relative to the reference-standard spectral energy distribution is determined.

To be able to use the reference-standard reflectance function in the manner known to the art for calculating the specimen reflectance factor function, the reference-standard reflectance function is adjusted based on the relative sensitivity of the two detection channels from the photo-detectors 4, 5 up to the spectrometer 9, for example, by multiplying with the relative sensitivity. The relative sensitivity can be wavelength-dependent.

The relative sensitivity can be determined, for example, by switching device 1 from the measuring position to the referencing position. This is done, for example, by turning the hollow body 3 around the same axis of rotation Q and by the same angle as when switching between the measuring position and the calibrating position, but in the opposite sense of rotation. This results in the first photo-detector 4 being directed at the same area of the diffusely scattering layer 15 at which the second detector 5 is directed in the measuring position. Thus, measuring light can now be detected for an adjustment spectral energy distribution, which defines the relative sensitivity of the detection channels in relation to the light-source spectral energy distribution in the measuring position (or alternatively, to the light-source spectral energy distribution detected by the second photo-detector 5 in the referencing position). To compensate for variations in brightness of the light source 6 during the detection of measuring light by the first photo-detector 4, reference light can be detected by the second photo-detector 5 in the known manner.

Alternatively, the relative sensitivity can be determined by placing reference standard 7 or an identical reference standard instead of specimen X and by using the first photo-detector in the measuring position to detect the spectral energy distribution, which is then compared (by component) to the spectral energy distribution detected by the second photo-detector. To compensate for variations in brightness of the light source 6 during the detection of the measuring light with the first photo-detector 4, reference light can be detected with the second photo-detector 5 and vice versa in the known manner.

For measuring the specimen properties, the control unit 21 switches device 1 into the measuring position via the drive (not shown). The signals emitted by the first photo-detector 4 in the measuring position are digitized by control unit 21 and stored as the specimen spectral energy distribution of the current measurement site. The signals emitted by the second photo-detector 5 in the measuring position are digitized by control unit 21 and stored as the light-source spectral energy distribution relative to the specimen spectral energy distribution. Based on these two spectral energy distributions and the adjusted reference-standard reflectance function, control unit 21 determines the specimen reflectance function of the currently measured site, for example, according to DE 195 28 855 A1.

By analyzing the specimen reflectance factor function, the control unit can, for example, monitor the value of a specific specimen property and compare it with a desired value or a desired interval. If any deviations are detected, it can, for example, record this and/or give out a visual and/or audible warning.

As in FIG. 1, the device 1 can be arranged in a common casing 2 and can be connected by optical fibers 19 to a spectrometer 22.

Figure 3:
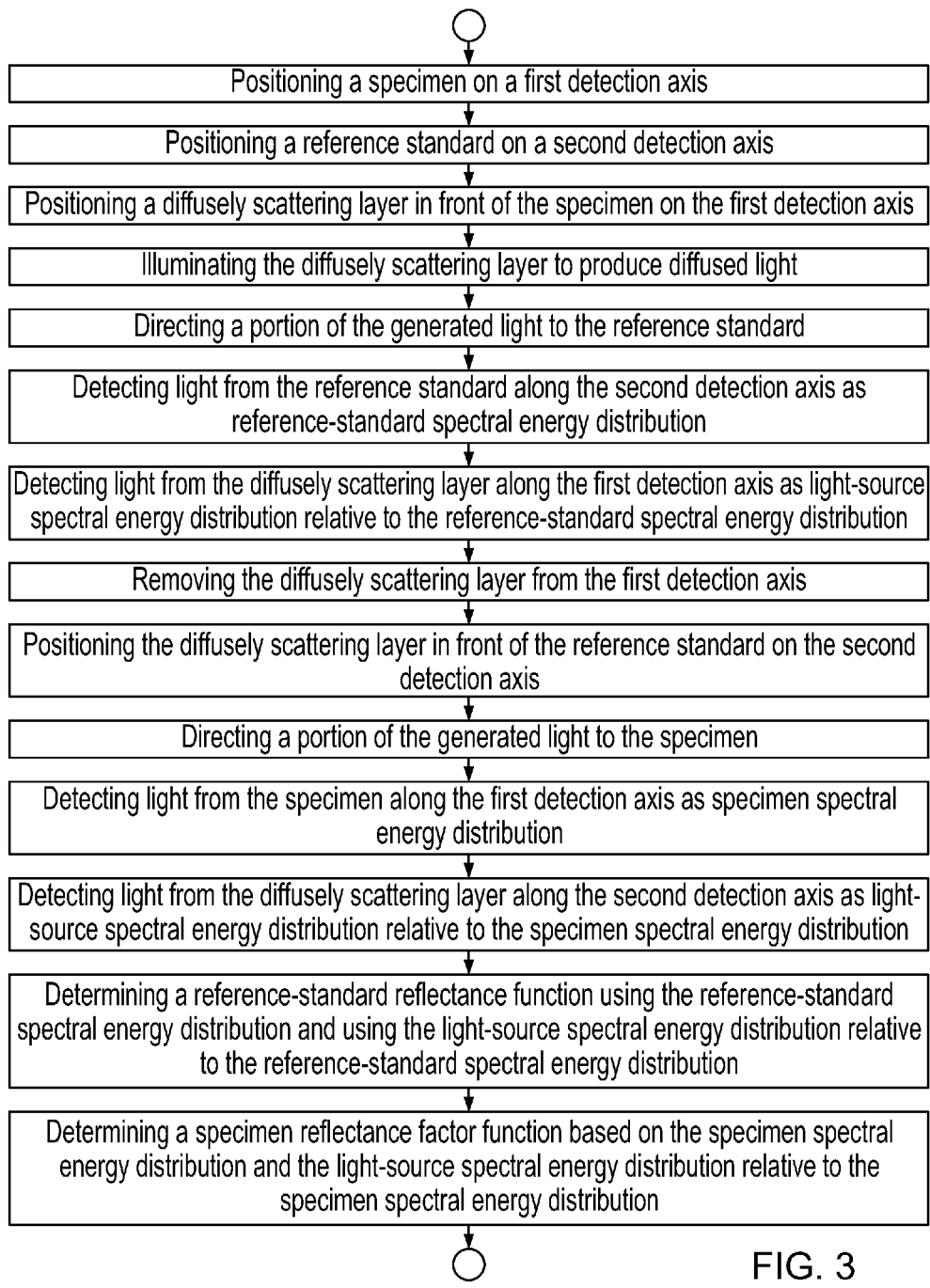
FIG. 3 shows a flow diagram of a measuring and calibration method for the second measuring device.

FIG. 3 shows a flowchart of a method for calibrating and measuring with a device as shown in FIG. 2.

Figure 4:
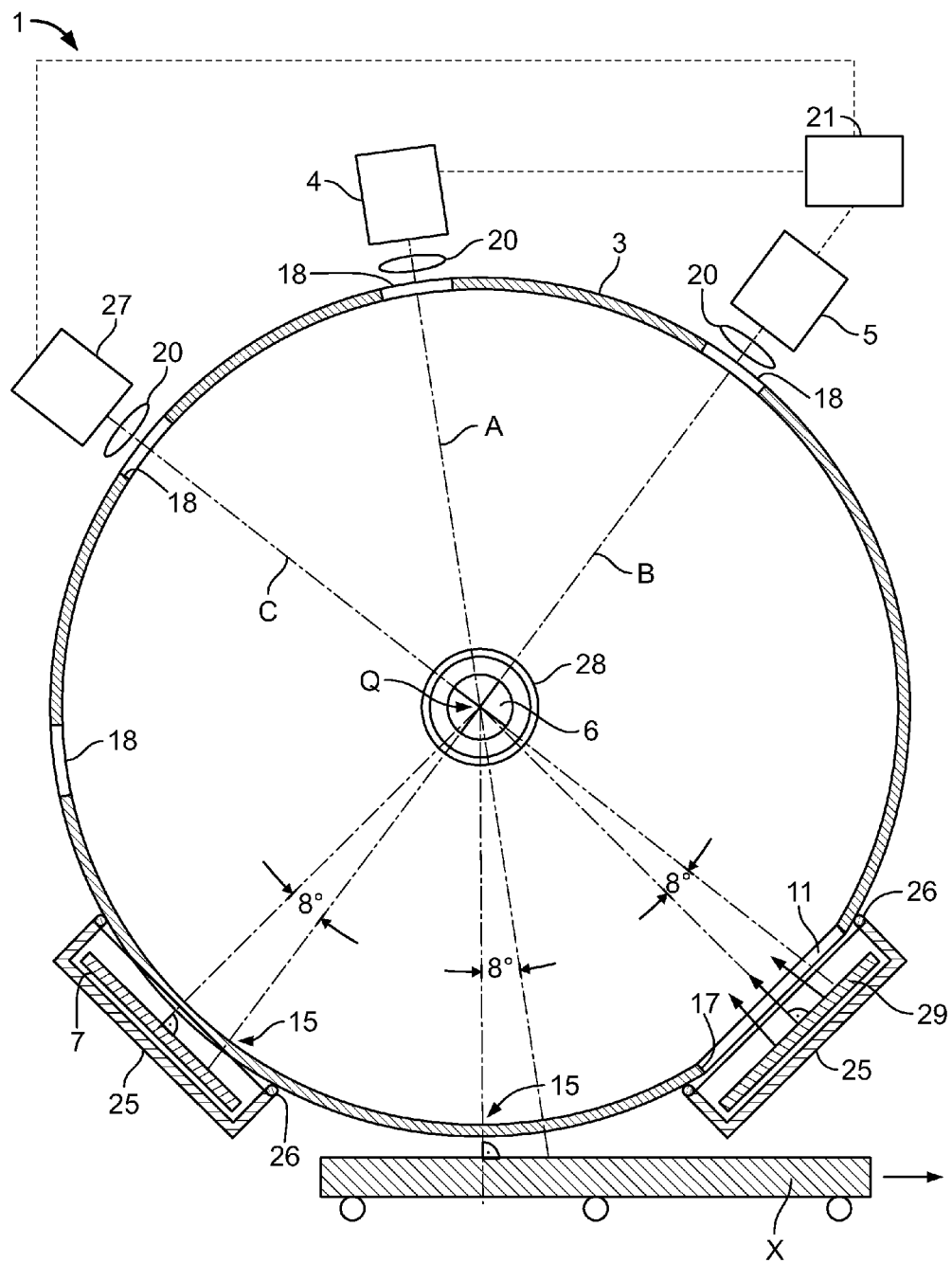
FIG. 4 shows a third measuring device in a third position.

FIG. 4 shows a device 1 similar to FIG. 2, which can be additionally switched into an auxiliary calibrating position. In the figure, device 1 is in this auxiliary calibrating position. In addition to the embodiment of the device according to FIG. 2, the illustrated device 1 includes a third photo-detector on the third detector hole 18, which is aligned along a third detection axis C, which, for example, is connected through a third optical shutter to the spectrometer, so that this can be switched on and off. In the auxiliary calibrating position, the light-exit opening 17 lies on the third detection axis C. An auxiliary reference standard 29 is arranged on the third detection axis C outside the hollow body 3, which, for example, has an average reflectance of 50%. The auxiliary reference standard 29 is arranged, for example, in a separate casing 25 with a seal 26, which includes a holder (not shown). Via the third photo-detector 27, measuring light from the auxiliary reference standard 29 can be detected in order to determine an additional reference-standard reflectance function. In the same position, reference light from the layer 15 can be detected by the first photo-detector 4 and by the second photo-detector 5 in order to determine the relative sensitivities of the detection channels.

Instead of a common spectrometer for all detection channels, all or at least some of the detection channels can also include a separate spectrometer. Determining the relative sensitivities for the adjustment of the respective spectral energy distributions is then carried out accordingly.

LIST OF REFERENCE NUMBERS

1 Measuring device
2 Casing
3 Hollow body
4 First photo-detector
5 Second photo-detector
6 Light source
7 Reference standard
8 Shutter
9 Spectrometer
10 Light-passage opening
11 Protective disc
12 Entrance slit
13 Imaging diffraction grid
14 Detector
15 Diffusely scattering layer
16 Light-inlet opening
17 Light-exit opening
18 Detector hole
19 Optical fiber
20 Optical probe
21 Control unit
22 Drive
23 Wall section
24 Holder
25 Casing
26 Seal
27 Third photo-detector
28 Shielding
29 Auxiliary reference standard
X Specimen
A First detection axis
B Second detection axis
C Third detection axis
Q Axis of rotation

What is claimed is:

1. A device, comprising:
 a hollow body having a light-exit opening configured to illuminate a specimen, an interior of the hollow body comprising a diffusely scattering layer;
 a light source configured to illuminate the diffusely scattering layer;
 a first photo-detector aligned along a first detection axis; and
 a second photo-detector aligned along a second detection axis,
 wherein:
  the device is switchable between a measuring position and a calibrating position;
  in the light measuring position:
   said light-exit opening lies on the first detection axis; and
   said light-exit opening does not lie on the second detection axis; and
  in the calibrating position:
   said light-exit opening lies on the second detection axis; and
   said light-exit opening does not lie on the first detection axis.

2. The device of claim 1, wherein the first photo-detector is aligned to receive:
 light entering through said light-exit opening into the hollow body in the measuring position; and
 light scattered by the diffusely scattering layer in the calibrating position.

3. The device of claim 1, wherein the second photo-detector is aligned to receive:
 light scattered by the diffusely scattering layer in the measuring position; and
 light entering through said light-exit opening into the hollow body in the calibrating position.

4. The device of claim 1, wherein the first and second photo-detectors and the first and second detection axes are fixed in space regardless of the device's position.

5. The device of claim 1, wherein:
 a first angle is defined by the second detection axis in the measuring position and the surface normal of the diffusely scattering layer at an intersection point of the second detection axis;
 a second angle is defined by the first detection axis in the calibrating position and the surface normal of the diffusely scattering layer at an intersection point of the first detection axis through the diffusely scattering layer; and
 the first and second angles are identical.

6. The device of claim 1, wherein a holder for a reference standard is arranged outside the hollow body, or the reference standard lies on the second detection axis.

7. The device of claim 1, wherein the device is also switchable into a referencing position in which the first detection axis and the second detection axis extend through the diffusely scattering layer.

8. The device of claim 1, further comprising a third photo-detector aligned along a spatially fixed third detection axis, wherein the device is switchable into an auxiliary calibrating position in which said light-exit opening lies on the third detection axis.

9. The device of claim 1, wherein the hollow body is rotatable to switch between the light measuring and calibration positions.

10. A device, comprising:
a hollow body having a light-exit opening configured to illuminate a specimen, an interior of the hollow body comprising a diffusely scattering layer;
a light source configured to illuminate the diffusely scattering layer;
a first photo-detector aligned along a first detection axis; and
a second photo-detector aligned along a second detection axis,
wherein:
the hollow body, including said light-exit opening and the first and second photo-detectors, is able to rotate about an axis different from the first detection axis to switch the device between a measuring position and a calibrating position;
the first photo-detector is aligned in the measuring and calibration positions to receive light that enters through said light-exit opening into the hollow body; and
the second photo-detector is aligned in the measuring and calibration positions to receive light scattered by the diffusely scattering layer.

11. The device of claim 10, wherein a holder for a reference standard is arranged outside the hollow body, or the reference standard is arranged so that in the calibrating position the reference standard lies on the first detection axis.

12. The device of claim 11, further comprising a shield, wherein the shield is between the specimen and at least one member selected from the group consisting of the holder and the reference standard.

13. The device of claim 12, wherein the shield comprises a casing around the holder and the reference standard, and the shield is open toward the hollow body.

14. The device of claim 12, wherein the shield protects the hollow body, the holder, the reference standard and the first and second photo-detectors from the specimen, the shield comprises a transparent opening in a region that contains said light-exit opening in the measuring position, and a transparent protective plate is disposed over the transparent opening.

15. The device of claim 12, wherein the shield is a common casing around the hollow body, the holder, the reference standard and the first and second photo-detectors.

16. The device of claim 11, wherein the holder is arranged so that a distance between the reference standard and said light-exit opening in the calibrating position is identical to a distance between the specimen and the light-passage opening in the measuring position.

17. The device of claim 10, wherein the first and second detection axes extend through the hollow body.

18. The device of claim 10, wherein in the measuring position the first detection axis is identical to a central axis of said light-exit opening or forms an angle of 8°.

19. The device of claim 10, wherein:
a first angle is defined by the second detection axis in the measuring position and the surface normal of the diffusely scattering layer at an intersection point of the second detection axis;
a second angle is defined by the first detection axis in the calibrating position and the surface normal of the diffusely scattering layer at an intersection point of the first detection axis through the diffusely scattering layer; and
the first and second angles are identical.

20. The device of claim 10, wherein the hollow body is an integrating sphere or an integrating tube.

21. A method for calibrating a device, comprising:
providing a device according to claim 1;
switching the device into a calibrating position;
passing light through said light-exit opening so that the second photo-detector receives the light as a reference-standard spectral energy distribution;
scattering light from the diffusely scattering layer so that the first photo-detector receives the scattered light as a light-source spectral energy distribution; and
based on the reference-standard spectral energy distribution and the light-source spectral energy distribution, determining a reference-standard reflectance function.

22. A method for calibrating a device, the method comprising:
providing a device according to claim 10;
switching the device into a calibrating position;
passing light through said light-exit opening so that the second photo-detector receives the light as a reference-standard spectral energy distribution;
scattering light from the diffusely scattering layer so that the first photo-detector receives the scattered light as a light-source spectral energy distribution; and
based on the reference-standard spectral energy distribution and the light-source spectral energy distribution, determining a reference-standard reflectance function.

23. The method of claim 22, further comprising:
after determining the reference-standard reflectance function, switching the device into the measuring position; and
subsequently:
passing light through said light-exit opening so that the first photo-detector receives the light as a specimen spectral energy distribution;
scattering light from the diffusely scattering layer so that the second photo-detector receives the scattered light as a second light-source spectral energy distribution; and
based on the specimen spectral energy distribution, the second light-source spectral energy distribution and the reference-standard spectral energy distribution, determining a specimen reflectance factor function.
and the specimen reflectance factor function is determined on the basis of these two spectral energy distributions and on the basis of the reference-standard reflectance function determined during the calibration.

24. An electronic system, comprising:
one or more processing devices; and
one or more machine-readable media configured to store instructions that are executable by the one or more processing devices to perform operations including a method which comprises:
providing a device according to claim 1;

switching the device into a calibrating position;

passing light through said light-exit opening so that the second photo-detector receives the light as a reference-standard spectral energy distribution;

scattering light from the diffusely scattering layer so that the first photo-detector receives the scattered light as a light-source spectral energy distribution; and based on the reference-standard spectral energy distribution and the light-source spectral energy distribution, determining a reference-standard reflectance function.

25. The method of claim 21, further comprising:

after determining the reference-standard reflectance function, switching the device into the measuring position; and subsequently:

passing light through said light-exit opening so that the first photo-detector receives the light as a specimen spectral energy distribution;

scattering light from the diffusely scattering layer so that the second photo-detector receives the scattered light as a second light-source spectral energy distribution; and based on the specimen spectral energy distribution, the second light-source spectral energy distribution and the reference-standard spectral energy distribution, determining a specimen reflectance factor function.

and the specimen reflectance factor function is determined on the basis of these two spectral energy distributions and on the basis of the reference-standard reflectance function determined during the calibration.

26. An electronic system, comprising:

one or more processing devices; and one or more machine-readable media configured to store instructions that are executable by the one or more processing devices to perform operations including a method which comprises:

providing a device according to claim 10;

switching the device into a calibrating position;

passing light through said light-exit opening so that the second photo-detector receives the light as a reference-standard spectral energy distribution;

scattering light from the diffusely scattering layer so that the first photo-detector receives the scattered light as a light-source spectral energy distribution; and based on the reference-standard spectral energy distribution and the light-source spectral energy distribution, determining a reference-standard reflectance function.

* * * * *

UNITED STATES PATENT AND TRADEMARK OFFICE
CERTIFICATE OF CORRECTION

| | | |
|---|---|---|
| PATENT NO. | : 8,830,473 B2 | Page 1 of 1 |
| APPLICATION NO. | : 13/486571 | |
| DATED | : September 9, 2014 | |
| INVENTOR(S) | : Joerg Margraf et al. | |

It is certified that error appears in the above-identified patent and that said Letters Patent is hereby corrected as shown below:

In the Claims

Col. 16, line 56, claim 23, delete "function." and insert -- function; --.

Col. 18, line 2, claim 25, delete "function." and insert -- function; --.

Signed and Sealed this
Sixteenth Day of December, 2014

Michelle K. Lee
*Deputy Director of the United States Patent and Trademark Office*